(12) United States Patent
Yeh et al.

(10) Patent No.: US 7,829,918 B2
(45) Date of Patent: Nov. 9, 2010

(54) FIELD EFFECT TRANSISTOR BASED SENSOR

(76) Inventors: Jer-Liang Andrew Yeh, No. 128, 12nd Neighborhood, Jiguang St., Central District, Taichung City (TW) 400; Shangjr Gwo, 101, Sec, 2 Kuang Fu Road, Hsinchu (TW) 30013

( * ) Notice: Subject to any disclaimer, the term of this patent is extended or adjusted under 35 U.S.C. 154(b) by 1 day.

(21) Appl. No.: 12/432,071

(22) Filed: Apr. 29, 2009

(65) Prior Publication Data
US 2010/0012987 A1   Jan. 21, 2010

(30) Foreign Application Priority Data
Jul. 16, 2008   (TW) .............................. 97127004 A

(51) Int. Cl.
*H01L 29/78*   (2006.01)
(52) U.S. Cl. ................. 257/253; 257/E29.255
(58) Field of Classification Search .................. 257/253, 257/E29.255
See application file for complete search history.

(56) References Cited

U.S. PATENT DOCUMENTS

| 5,833,824 A | 11/1998 | Benton |
| 7,361,946 B2 * | 4/2008 | Johnson et al. ............. 257/253 |
| 2008/0203431 A1 | 8/2008 | Garcia et al. |

* cited by examiner

*Primary Examiner*—Trung Dang
(74) *Attorney, Agent, or Firm*—Thomas, Kayden, Horstemeyer & Risley, LLP.

(57) ABSTRACT

The invention discloses a FET based sensor. The FET based sensor according to an embodiment of the invention includes a substrate, an InN material layer, a source terminal and a drain terminal. The InN material layer is formed over the substrate and has an upper surface. The upper surface thereon provides an analyte sensing region. The InN material layer serves as a current channel between the source terminal and the drain terminal. Thereby, ions adsorbed by the analyte sensing region induce a variation of a current flowing through the current channel, and the variation is further interpreted as a characteristic of the analyte.

24 Claims, 6 Drawing Sheets

FIELD EFFECT TRANSISTOR BASED SENSOR

CROSS-REFERENCE TO RELATED APPLICATION

This application claims priority to Taiwan Application Serial Number 097127004, filed Jul. 16, 2008, which is incorporated herein by reference.

BACKGROUND OF THE INVENTION

1. Field of the Invention

The invention relates to a field effect transistor (FET) based sensor. More particularly, the invention relates to a FET based sensor with high performance sensitivity and response time.

2. Description of the Prior Art

The ion-sensitive field effect transistor (ISFET) is an electrochemical sensing component disclosed by Piet Bergveld in 1970. The ISFET realizes the combination of minimization and automatic measuring. An ISFET is similar to a metal oxide semiconductor field effect transistor (MOSFET), but the ISFET does not have a conductive gate terminal. Instead, an ion-sensitive membrane is placed over the gate or channel region of the ISFET and is exposed to a sample solution. The wiring of the ISFET is not attached to the gate terminal like a MOSFET, but the wiring of the ISFET is attached to a reference electrode. The reference electrode is separated from the ion-sensitive membrane by the solution. The ion-sensitive membrane modulates the gate charge, and thus the potential difference between the gate and the reference electrode, as a function of the ion concentration in the sample solution. One or more operating characteristics of the ISFET are then measured and used to calculate the ion concentration. Compared to the metal-oxide-semiconductor field effect transistor (MOSFET) utilized in common integrated circuits, the main difference between the ISFET and the MOSFET is that the ISFET utilizes the ion-detecting layer and the electrolyte to substitute the gate terminal of the MOSFET. With the ion selecting function and the characteristic of FET, the ISFET is a new sensor combining electrochemistry and semiconductor.

The use of ISFET for sensing ion is known. For example, the U.S. Pat. No. 5,833,824 discloses such a sensor. One application of the ISFET sensors is in the process control of the food and beverage. It is because that the traditional pH glass sensor is unsuitable and prohibited from the food and beverage.

It is also known that different materials have different sensing characteristics when used as ion-sensing membranes of pH ISFETs. In 1970 Bergveld of the Technical University Twente (TH Twente) described the principle of the ISFET. The ISFET includes semi-conductor material, for example p-type silicon, which is provided with an oxide surface, such as silicon dioxide ($SiO_2$), silicon nitride ($Si_3N_4$), alumina ($Al_2O_3$), zirconia ($ZrO_2$) and tantalum oxide ($Ta_2O_5$). However, the strength of the ion-sensing membrane of the pH ISFET is usually not enough. The ion-sensing membrane of the pH ISFET is going to be etched under some detection processes, for instance, the Cleaned In Place (CIP) process with a 2% NaOH solution at 85° C.

Besides the pH ISFETs, there are several types of ISFET structures. For example, a high-electron-mobility transistor (HEMT) can serve as an ISFET. The U.S. patent Pub. No. 2008/0203431A1 discloses such a sensor. Please refer to FIG. 1. FIG. 1 is a sectional view illustrating an ISFET 1 in prior art. The ISFET 1 in FIG. 1 is an AlGaN/GaN high-electron-mobility transistor. As shown in FIG. 1, the ISFET 1 includes a substrate 10, an AlN layer 11, GaN layers (12, 14), an AlGaN layer 13, a source terminal 15 and a drain terminal 16. The AlN layer 11 serves as a nucleation layer. The GaN layer 12 serves as a buffer layer. Therein, a two-dimensional electron gas (2DEG) 17 is formed at the interface between the GaN layer 12 and the AlGaN layer 12, and more particularly, located on side by the GaN layer 12. As shown in FIG. 1, the exposed gate area 140 can detect the attached ions, such that the surface potential of the ISFET 1 is modified to affect the density of the 2DEGs 17, so as to change the source-to-drain current flow.

By aforesaid interaction, the AlGaN/GaN HEMT can server as an ISFET. However, the sensitivity and the response time of the AlGaN/GaN HEMT-type ISFET is not ideal. It is not sensitive and fast enough to achieve the real-time detection and high sensitivity needed in modern sensor technologies.

Therefore, the invention discloses an ISFET sensor with high sensitivity and short response time, so as to solve said problems.

SUMMARY OF THE INVENTION

A scope of the invention is to provide a FET based sensor.

According to a first embodiment, the FET based sensor includes a substrate, an InN material layer, a source terminal and a drain terminal.

The InN material layer is formed over the substrate. The InN material layer has an upper surface. An analyte sensing region is provided on the upper surface. Besides, the InN material layer functions as a current channel between the source terminal and the drain terminal. Accordingly, the analyte adsorbed by the analyte sensing region induces a variation of a current, which goes through the current channel. The variation being further interpreted as a characteristic of the analyte.

According to a second embodiment, the invention discloses another FET based sensor. To be noticed that, the FET based sensor of the second embodiment utilizes an InGaN material layer to substitute the InN material layer in the first embodiment. The chemical formula of the InGaN of the invention is expressed as $In_xGa_{(1-x)}N$, where $x > 0.4$.

The advantage and spirit of the invention may be understood by the following recitations together with the appended drawings.

BRIEF DESCRIPTION OF THE APPENDED DRAWINGS

DETAILED DESCRIPTION OF THE INVENTION

Figure 1:
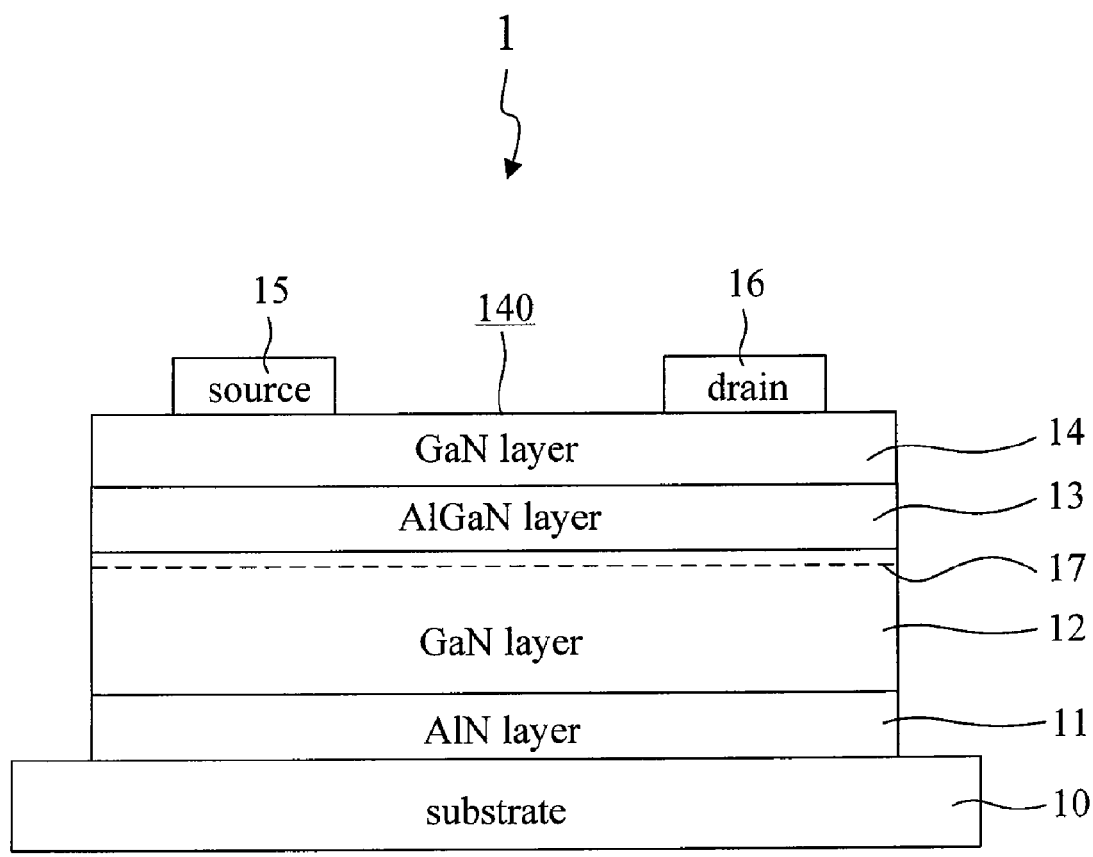
FIG. 1 is a sectional view illustrating an ISFET in prior art.
Figure 2:
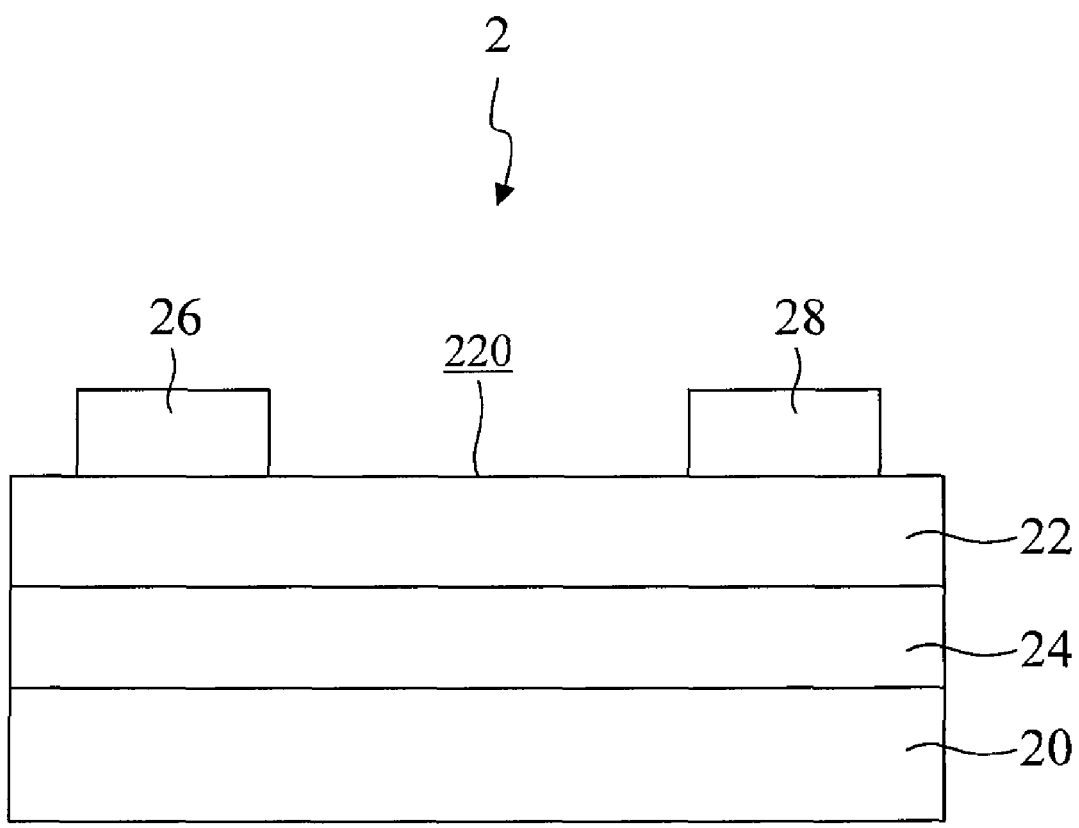
FIG. 2 is a sectional view illustrating a FET based sensor according to a first embodiment of the invention.

Please refer to FIG. 2. FIG. 2 is a sectional view illustrating a FET based sensor 2 according to a first embodiment of the invention. As shown in FIG. 2, the FET based sensor 2 includes a substrate 20, an InN material layer 22, a source terminal 26 and a drain 28.

In practical applications, the substrate 20 can be made of, but not limited to, Si, GaN, AlN, sapphire or SiC.

The InN material layer 22 is formed over the substrate 20 and has an upper surface 220. In practical application, the FET based sensor 2 further includes a buffer layer 24. The buffer layer 24 is formed between the substrate 20 and the InN material layer 22, for assisting the epitaxy process of the InN material layer 22. In this embodiment, the buffer layer 24 can be made of AlN.

With the developing epitaxy technology, the unique optical and electrical characteristic of the InN material is recently figured out by researchers. For example, the intrinsic InN material has high free-electron concentration, over $10^{18}$ cm$^{-3}$ in general. Beside, based on the experimental verification, the surface of the InN material has an intrinsic electron-accumulation phenomenon. The electron-accumulation phenomenon of the InN material is unique in III-IV group semiconductors. Once, the semiconductor industry tries to remove this electron-accumulation with some physical or chemical process, but in vain. Besides, the density of the donor state with positive charges in the InN material reaches $10^3$ cm$^{-2}$, highest in III-IV group semiconductors.

Because the InN material has high density of the surface donor state, it is suitable to be implemented in a sensing application. For example, the state with positive charges of the InN material may attract ions in the solution. Therefore, the ions may attach on the surface of the InN material. In other words, the upper surface 220 of the InN material layer 22 can provides an analyte sensing region. In practical application, the analyte can be an ion, a chemical molecule or a biological molecule. Besides, the analyte can be solid, liquid or gaseous.

The source terminal 26 and the drain terminal 28 can be formed on the InN material layer 22. Practically, the source terminal 26 and the drain terminal 28 are both made of a material capable of forming an ohmic contact, for example, Au/Ti alloy, Au or Al. Besides providing the analyte sensing region on the upper surface, the InN material layer functions as a current channel between the source terminal 26 and the drain terminal 28 at the same time. Accordingly, the adsorbed analyte on the analyte sensing region induce a variation of a current, i.e. the source-to-drain current $I_{DS}$, flowing through the current channel. Afterward, the variation of the current is further interpreted as a characteristic of the analyte, e.g. the concentration.

For example, when the FET based sensor 2 in the invention is placed into a solution with negative ions under test, the negative ions may attach on the ion sensing region and dispel some electrons accumulated on the surface of the InN material layer, such that it may reduce the current flowing through the current channel. Basically, the variation of the current is related to the concentration of the ions. With high concentration of the ions, it leads to a large decrease of the current because there are more ions attached on the ion sensing region. Therefore, the FET based sensor 2 according to the invention may analyze the concentration of the ions based on the variation of the current $I_{DS}$.

Figure 3:
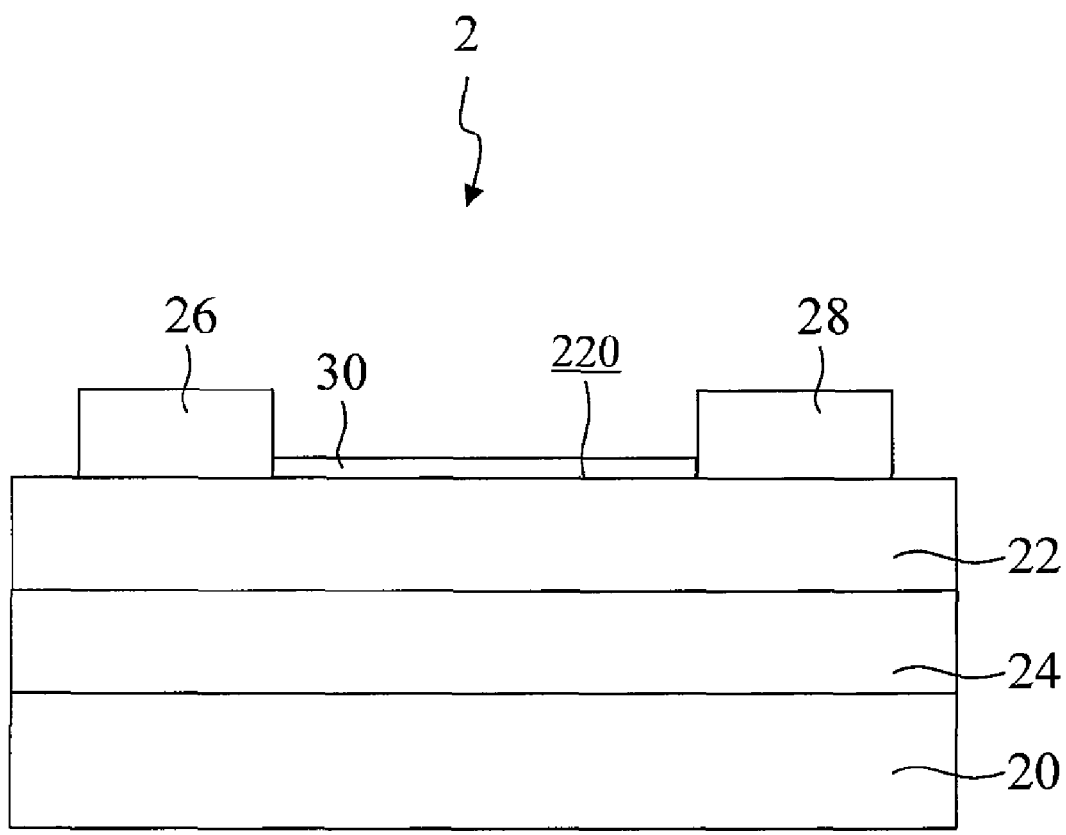
FIG. 3 is a sectional view illustrating the FET based sensor further including an analyte selective film.

Please refer to FIG. 3. FIG. 3 is a sectional view illustrating the FET based sensor 2 further including an analyte selective film 30. As shown in FIG. 3, the analyte selective film 30 is formed over the upper surface 220 of the InN material layer 22. The analyte selective film 30 may selective attach some particular particles under test, for detecting molecules, e.g. proteins, antibodies, antigens or some chemical particles. Therefore, the FET based sensor 2 can function as a chemical sensor, a biological sensor, a biochemical sensor, a physical parameter detector and for some pathological applications.

In the aforementioned embodiment, when the FET based sensor 2 is placed in the solution with ions under test, the ions in the solution may react with the source terminal 26 and the drain terminal 28 (e.g. etching the terminals), such that the current flowing through the current channel will be unstable.

Figure 4:
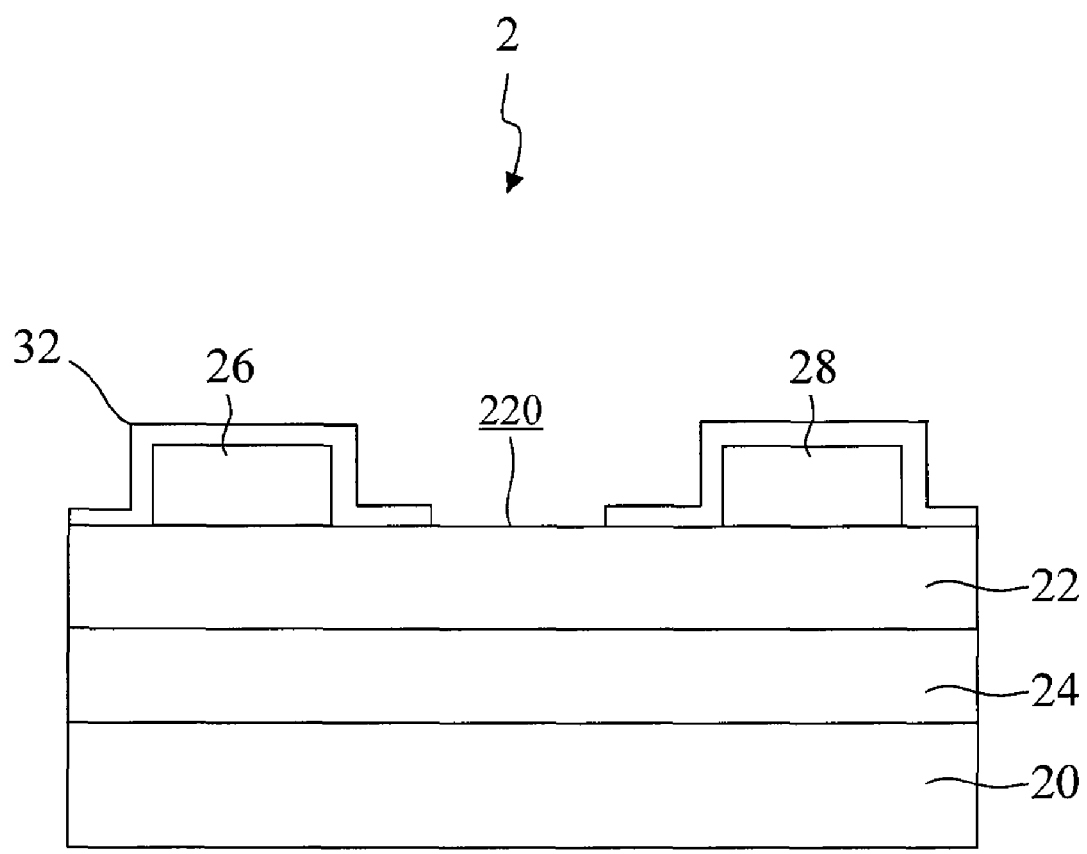
FIG. 4 is a sectional view illustrating the FET based sensor according to the invention further including a passivation layer.

Please refer to FIG. 4. FIG. 4 is a sectional view illustrating the FET based sensor 2 according to the invention further including a passivation layer 32. In practical applications, the passivation layer 32 can be made of, but not limited to, $Si_3N_4$ or epoxy.

In order to solve the unstable problem of the current, the passivation layer 32 in FIG. 4 can be disposed to cover the source terminal 26, the drain terminal 28 and the upper surface 220 of the InN material layer 22 except the analyte sensing region. The passivation layer 32 is used for isolating the ions in the solution from the source terminal 26 and the drain terminal 28, so as to elevate the current stability. Therefore, the passivation layer 32 can elevate the stability of the analyte sensing of the FET based sensor 2 according to the invention.

On the other hand, in another embodiment, a thermal oxidation process or an oxygen-doping process is applied to part of the InN material layer 22 adjacent to the upper surface 220 to form an $In_2O_3$ or $InO_x$ surface layer.

Figure 5:
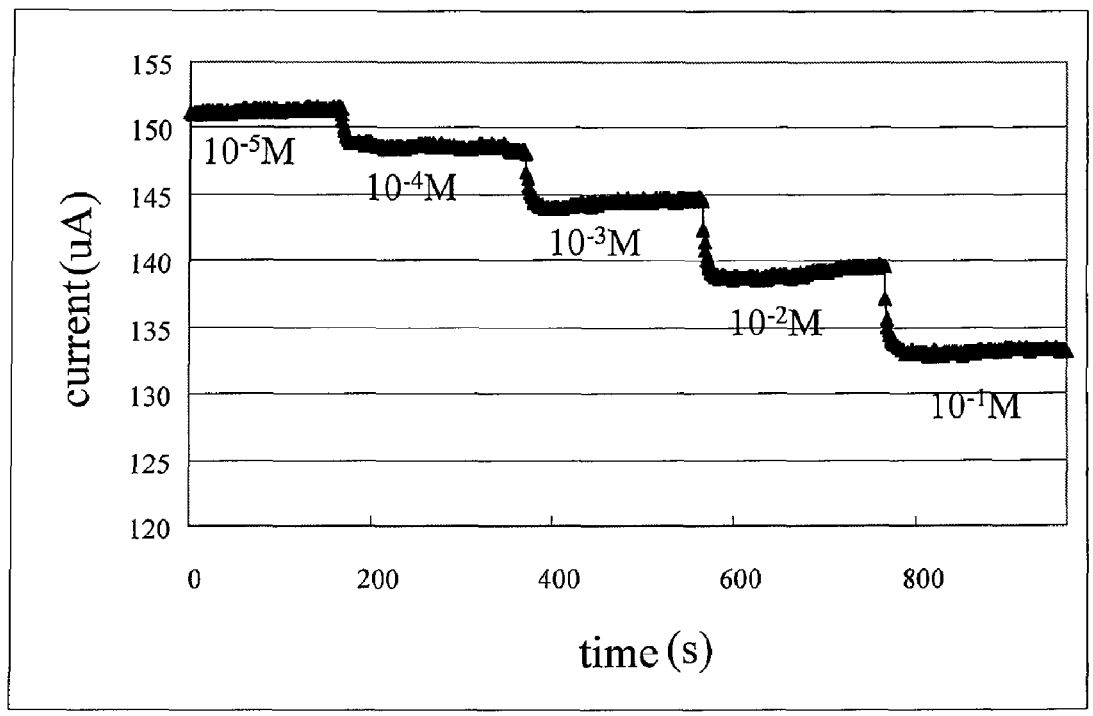
FIG. 5 is a relation plot illustrating the timing relation between the current $I_{DS}$ and the concentration of $Cl^-$ ions.

To measure the sensing performance of the FET based sensor 2 according to the invention, in an embodiment, the FET based sensor 2 is placed in a KCl solution for sensing the concentration of Cl$^-$ ions. Please refer to FIG. 5. FIG. 5 is a relation plot illustrating the timing relation between the current $I_{DS}$ and the concentration of Cl$^-$ ions.

As shown in FIG. 5, in the measuring period, the concentration of Cl$^-$ ions decreases from $10^{-5}$ M to $10^{-1}$ M. When the concentration of Cl$^-$ ions is raised, there are more ions attached on the ion sensing region, and more electrons accumulated on the surface of the InN material layer are dispelled, such that the concentration of the surface donor state of the InN semiconductor layer is reduced. The free-electrons dispelling can be equivalent to the enlarging of the impedance of the current channel between the source terminal 26 and the drain terminal 28, therefore, the current flowing through the current channel is reduced. Additionally, the respond time of the FET based sensor 2 in the invention to the variation of Cl$^-$ ions can be shorter than 10 seconds. In comparison, the AlGaN/GaN HEMT sensor in prior art has a response time between 20 to 30 seconds. To be concluded that, the FET based sensor 2 according to the invention responses faster.

Figure 6:
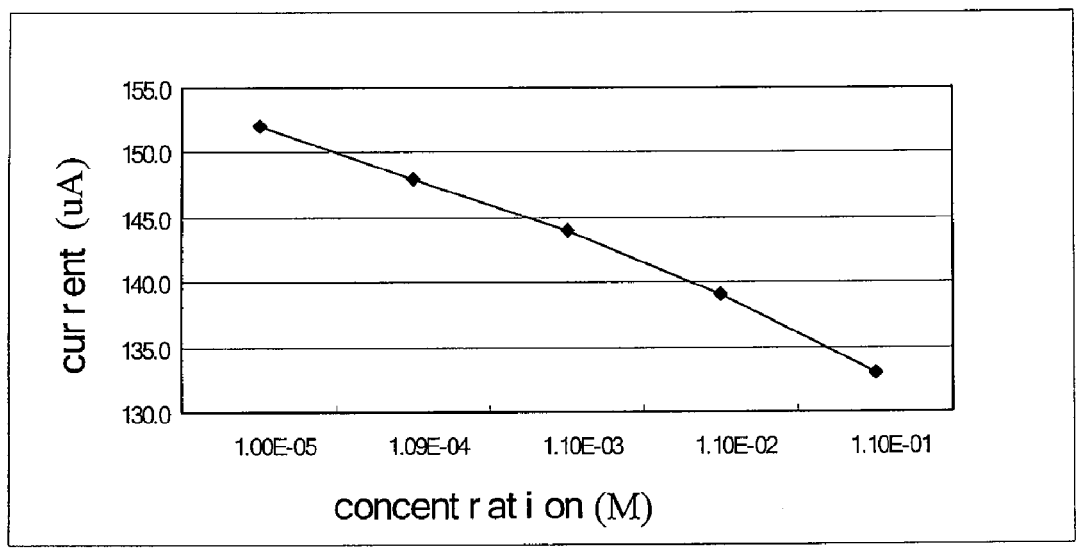
FIG. 6 is a relation plot illustrating the relation between the current $I_{DS}$ and the concentration of $Cl^-$ ions.

Please refer to FIG. 6. FIG. 6 is a relation plot illustrating the relation between the current $I_{DS}$ and the concentration of Cl$^-$ ions. Obviously, the current $I_{DS}$ may change linearly corresponding to the varying concentration of Cl$^-$ ions. Through the quantitative analysis, e.g. linear interpolation, the FET based sensor 2 in the invention may precisely measure the concentration of Cl$^-$ ions. In the experiment of the sensitivity of the FET based sensor 2, the current $I_{DS}$ varies 3% when the concentration of Cl$^-$ ions changes $10^{-1}$ M. Compared with the AlGaN/GaN HEMT sensor, the FET based sensor 2 in the invention has higher sensitivity.

Generally, the thinner InN material layer 22 can contribute to the higher sensitivity of the FET based sensor 2. In an embodiment, when the thickness of the InN semiconductor layer is smaller than 20 nm, the ion sensing region of the InN semiconductor layer can absorb both the positive and negative ions. In this case, the thickness of the InN semiconductor layer is so thin that other semiconductor layers below the InN layer may affect the surface state of the InN layer, such that the positive ions may attaches on the InN layer as well.

According to a second embodiment, the invention discloses another FET based sensor. To be noticed that, the FET based sensor of the second embodiment utilizes an InGaN material layer to substitute the InN material layer in the first embodiment. To be noticed that, the chemical formula of the InGaN of the invention is expressed as $In_xGa_{(1-x)}N$, where x>0.4. In other words, once if the ratio of between In and InGaN is over 40%, the InGaN material layer may have the same sensing performance as the InN material layer in aforesaid embodiments. Besides, the structural implantation or the operating theory of the FET based sensor in the second embodiment is similar to the first embodiment, please refer to the first embodiment.

Compared with prior art, with the unique electron accumulation within the InN material, the FET based sensor according to the invention may utilize InN semiconductor layer as the source-to-drain current channel and the analyte sensing region. Therefore, the FET based sensor in the invention can function as a sensor for various proposes, e.g. a chemical sensor and a biochemical sensor. At the same time, the FET based sensor in the invention can perform with high sensitivity and fast response time.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A field effect transistor based sensor, comprising:
    a substrate;
    an InN material layer, the InN material layer being formed over the substrate and having an upper surface, an analyte sensing region being provided on the upper surface;
    a source terminal; and
    a drain terminal, the InN material layer functioning as a current channel between the source terminal and the drain terminal, the analyte adsorbed by the analyte sensing region inducing a variation of a current flowing through the current channel, the variation being further interpreted as a characteristic of the analyte.

2. The field effect transistor based sensor of claim 1, wherein a thickness of the InN material layer is substantially smaller than 20 nm.

3. The field effect transistor based sensor of claim 1, wherein the variation is further interpreted as a concentration of the analyte.

4. The field effect transistor based sensor of claim 1, further comprising:
    an analyte selective film, the analyte selective film being formed over the analyte sensing region.

5. The field effect transistor based sensor of claim 1, further comprising:
    a buffer layer, the buffer layer being formed between the substrate and the InN material layer.

6. The field effect transistor based sensor of claim 5, wherein the buffer layer is made of AlN.

7. The field effect transistor based sensor of claim 1, further comprising:
    a passivation layer, the passivation layer covering the source terminal, the drain terminal and the upper surface of the InN material layer except the analyte sensing region.

8. The field effect transistor based sensor of claim 1, wherein a thermal oxidation process or an oxygen-doping process is applied to part of the InN material layer adjacent to the upper surface to form an $In_2O_3$ or $InO_x$ surface layer.

9. The field effect transistor based sensor of claim 1, wherein the source terminal and the drain terminal are both made of a material capable of forming an ohmic contact.

10. The field effect transistor based sensor of claim 1, wherein the substrate is made of a material selected from the group consisting of silicon, GaN, AlN, sapphire and SiC.

11. The field effect transistor based sensor of claim 1, wherein the analyte is solid, liquid or gaseous.

12. The field effect transistor based sensor of claim 1, wherein the analyte is selected from the group consisting of an ion, a chemical molecule and a biologic molecule.

13. A field effect transistor based sensor, comprising:
    a substrate;
    an InGaN material layer, the InN material layer being formed over the substrate and having an upper surface, an analyte sensing region being provided on the upper surface, a chemical formula of InGaN being expressed as $In_xGa_{(1-x)}N$, where x>0.4;
    a source terminal; and
    a drain terminal, the InGaN material layer functioning as a current channel between the source terminal and the drain terminal, the analyte adsorbed by the analyte sensing region inducing a variation of a current flowing through the current channel, the variation being further interpreted as a characteristic of the analyte.

14. The field effect transistor based sensor of claim 13, wherein a thickness of the InGaN material layer is substantially smaller than 20 nm.

15. The field effect transistor based sensor of claim 13, wherein the variation is further interpreted as a concentration of the analyte.

16. The field effect transistor based sensor of claim 13, further comprising:
    an analyte selective film, the analyte selective film being formed over the analyte sensing region.

17. The field effect transistor based sensor of claim 13, further comprising:
    a buffer layer, the buffer layer being formed between the substrate and the InGaN material layer.

18. The field effect transistor based sensor of claim 17, wherein the buffer layer is made of AlN.

19. The field effect transistor based sensor of claim 13, further comprising:
    a passivation layer, the passivation layer covering the source terminal, the drain terminal and the upper surface of the InGaN material layer except the analyte sensing region.

20. The field effect transistor based sensor of claim 13, wherein a thermal oxidation process or an oxygen-doping process is applied to part of the InGaN material layer adjacent to the upper surface to form an $InGaN_xO_y$ or $InGaO_x$ surface layer.

21. The field effect transistor based sensor of claim 13, wherein the source terminal and the drain terminal are both made of a material capable of forming an ohmic contact.

22. The field effect transistor based sensor of claim 13, wherein the substrate is made of a material selected from the group consisting of silicon, GaN, AlN, sapphire and SiC.

23. The field effect transistor based sensor of claim 13, wherein the analyte is solid, liquid or gaseous.

24. The field effect transistor based sensor of claim 13, wherein the analyte is selected from the group consisting of an ion, a chemical molecule and a biologic molecule.

* * * * *